United States Patent [19]

Bird

[11] 4,044,763
[45] Aug. 30, 1977

[54] VENTILATOR AND METHOD

[76] Inventor: Forrest M. Bird, 212 NW. Cerritos, Palm Springs, Calif. 92262

[21] Appl. No.: 593,667

[22] Filed: July 7, 1975

[51] Int. Cl.² .................................... A61M 16/00
[52] U.S. Cl. ......................................... 128/145.8
[58] Field of Search ............. 128/145.5, 145.6, 145.8, 128/142.3, 142.2, 142, 203

[56] References Cited

U.S. PATENT DOCUMENTS

| | | | |
|---|---|---|---|
| 3,434,471 | 3/1969 | Liston | 128/145.8 |
| 3,537,448 | 11/1970 | Liston | 128/145.5 |
| 3,881,480 | 5/1975 | Lafourcade | 128/145.8 |

Primary Examiner—Robert W. Michell
Assistant Examiner—Henry J. Recla
Attorney, Agent, or Firm—Flehr, Hohbach, Test, Albritton & Herbert

[57] ABSTRACT

Ventilator having an inhalation phase and an exhalation phase in its operative cycle for use with a source of gas under pressure. A master sequencing cartridge having an inlet adapted to be connected to a source of gas under pressure and an outlet is provided. The cartridge has a valve member movable between open and closed positions to control the flow of gas from the inlet to the outlet. The cartridge is provided with a diaphragm capable of operating under differentials in pressure for causing movement of said valve member. A breathing circuit outlet is provided and tubing is provided for coupling the breathing circuit outlet to the outlet of the master sequencing cartridge. A volume-rate control valve assembly is provided for controlling the movement of the valve member of the master sequencing cartridge between open and closed positions. The volume/rate control valve assembly has an inlet and an outlet with tubing coupling the inlet of the control valve assembly to the outlet of the master sequencing cartridge and tubing connecting the inlet to the diaphragm of the cartridge whereby the timing for moving the valve member between open and closed positions is determined by the rate of flow of gases through the volume/rate control valve assembly.

8 Claims, 6 Drawing Figures

THE DYNAMIC INSPIRATORY PHASE

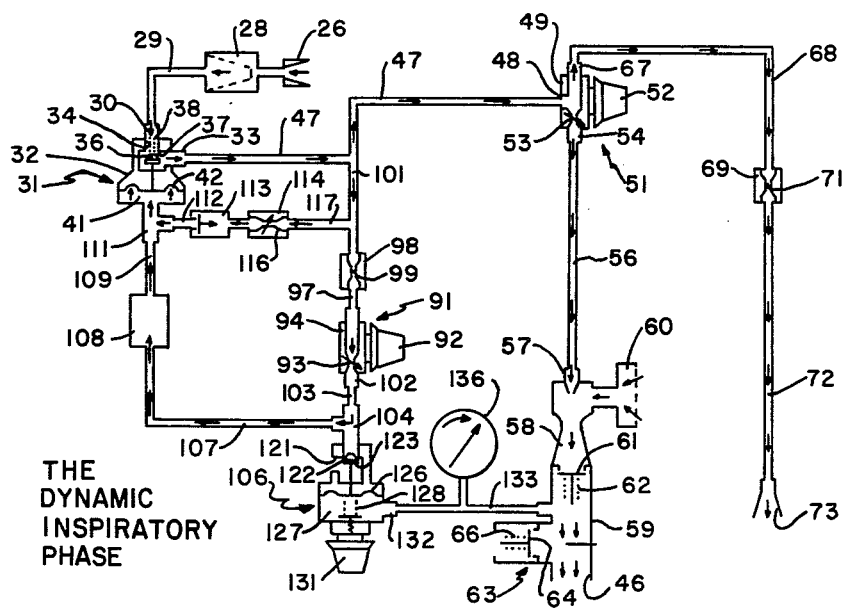
FIG.—3
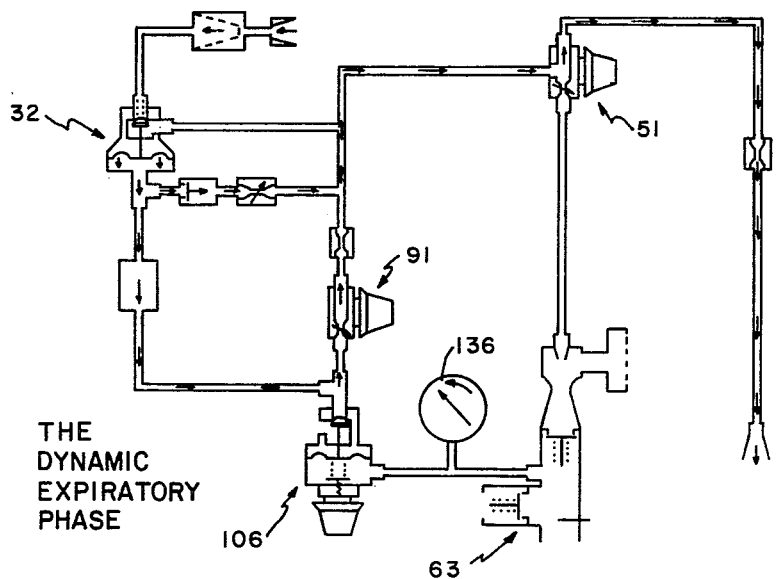
FIG.—4
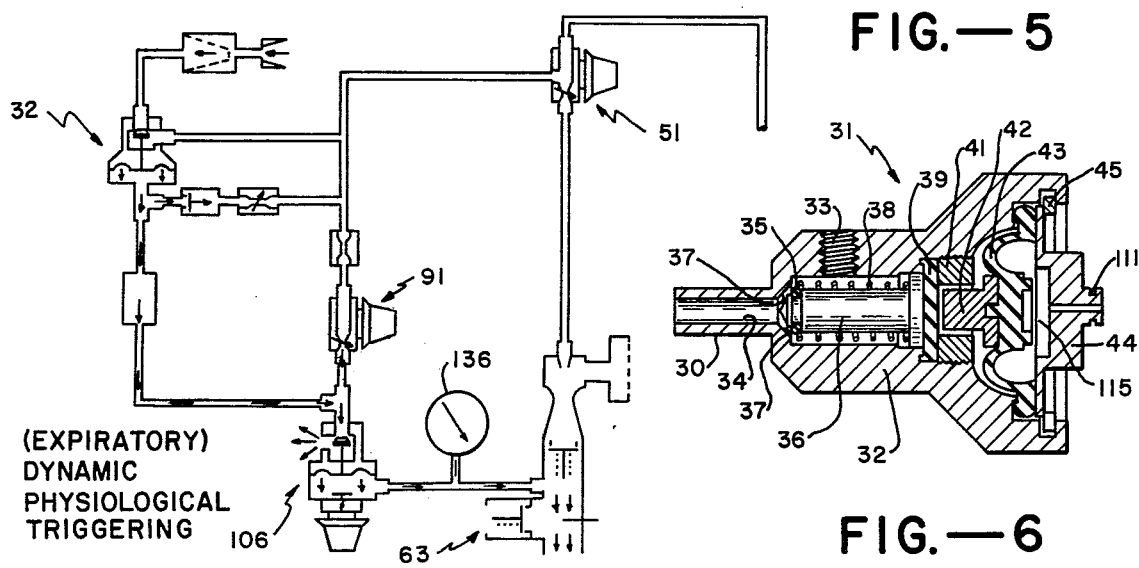
FIG.—5
FIG.—6

VENTILATOR AND METHOD

BACKGROUND OF THE INVENTION

Emergency medicine has emerged as a major specialty during recent years and involves initial management at the site of physiological failure or trauma, the transport to a formal medical facility and emergency room care. In connection with such emergency medicine, there has arisen a need to provide ventilatory care. Because of the complexities created by patients sized from a small infant to a large adult with their vast differences in pulmonary tidal volumes and the rates desired, it has been very difficult to provide a satisfactory ventilator which can meet these problems and at the same time be simple enough to operate so that it can be utilized by medical transport crews, paramedics and the like without unduly compromising the requirement of the patient being cared for. There is, therefore, a need for a ventilator which can meet these requirements.

SUMMARY OF THE INVENTION AND OBJECTS

The ventilator has an inhalation phase and an exhalation phase in its operative cycle and is for use with a source of gas under pressure. A master sequencing cartridge is provided having an inlet adapted to be connected to the source of gas under pressure and an outlet. It has a valve member movable between open and closed positions to control the flow of gas from the inlet to the outlet. Diaphragm means is coupled to the valve member for moving the same between open and closed positions. The ventilator is provided with a breathing circuit outlet and means is provided coupling the breathing circuit outlet to the outlet of the master sequencing cartridge. Means is provided for controlling the movement of the valve member between open and closed positions of the master sequencing cartridge and includes a volume/rate control valve assembly having an inlet and an outlet. Means is provided for coupling the inlet of the control valve assembly to the outlet of the master sequencing cartridge. Means is also provided for connecting the inlet to the diaphragm so that gas under pressure can be supplied to the diaphragm to move the valve member between said open and closed positions. When desired, a balance reservoir is provided for controlling the flow from the volume/rate control valve assembly to the diaphragm to smooth the operation of the master sequencing cartridge.

In general, it is an object of the present invention to provide a ventilator and method in which a single control can be utilized to provide control capabilities ranging over a very wide range.

Another object of the invention is to provide a ventilator of the above character which is capable of being used for human beings of all ages.

Another object of the invention is to provide a ventilator and method of the above character which is particularly useful in emergency medicine.

Another object of the invention is to provide a ventilator and method of the above character in which additional gas under pressure is supplied to the patient upon demand of the patient.

Another object of the invention is to provide a ventilator and method of the above character in which time cycling is utilized.

Additional objects and features of the present invention will appear from the following description in which the preferred embodiment is set forth in detail in conjunction with the accompanying drawing.

BRIEF DESCRIPTION OF THE DRAWING

FIG. 3 is a schematic diagram of the various components of the ventilator shown in FIG. 2 and showing the flow of gases during the dynamic inspiratory phase.

FIG. 4 is a schematic diagram similar to FIG. 3 but showing the flow of gases during the dynamic expiratory phase.

FIG. 5 is a schematic diagram similar to FIGS. 3 and 4 showing the flow of gases during dynamic physiological triggering.

FIG. 6 is a cross-sectional view of the normally open master sequencing cartridge shown in FIGS. 3, 4 and 5.

DESCRIPTION OF PREFERRED EMBODIMENT

Figure 1:
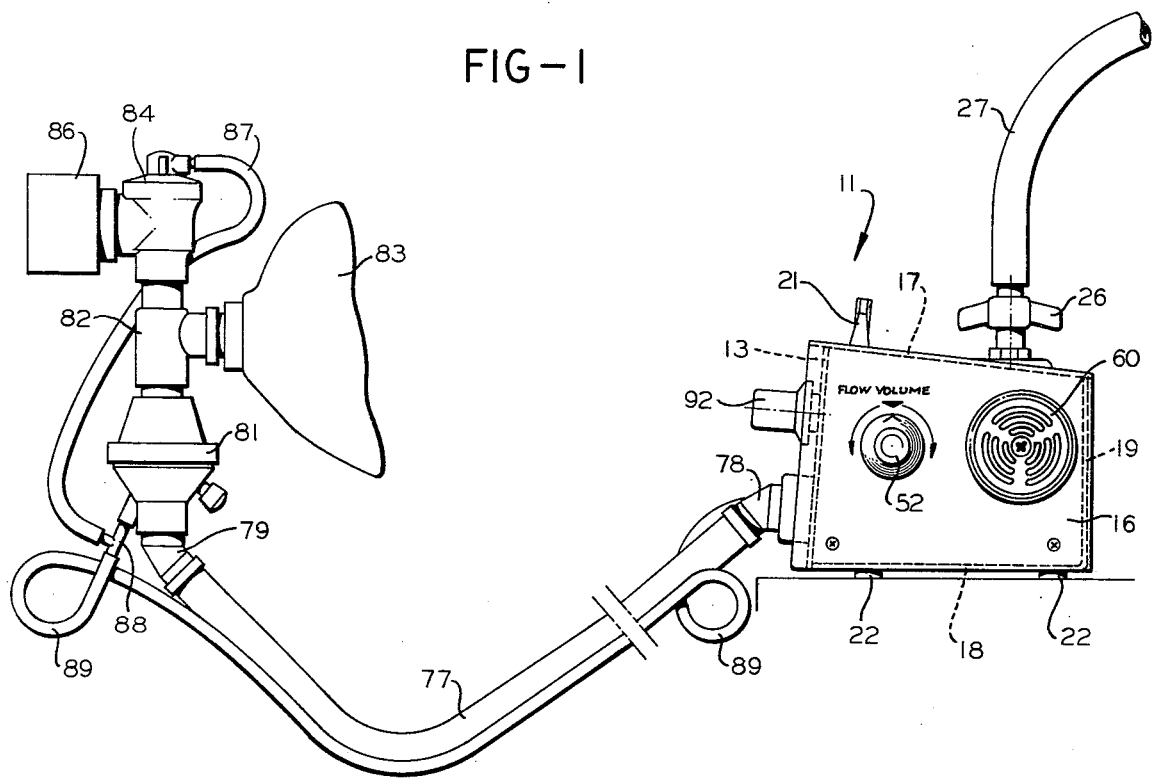
FIG. 1 is a front elevational view of a ventilator incorporating the present invention.
Figure 2:
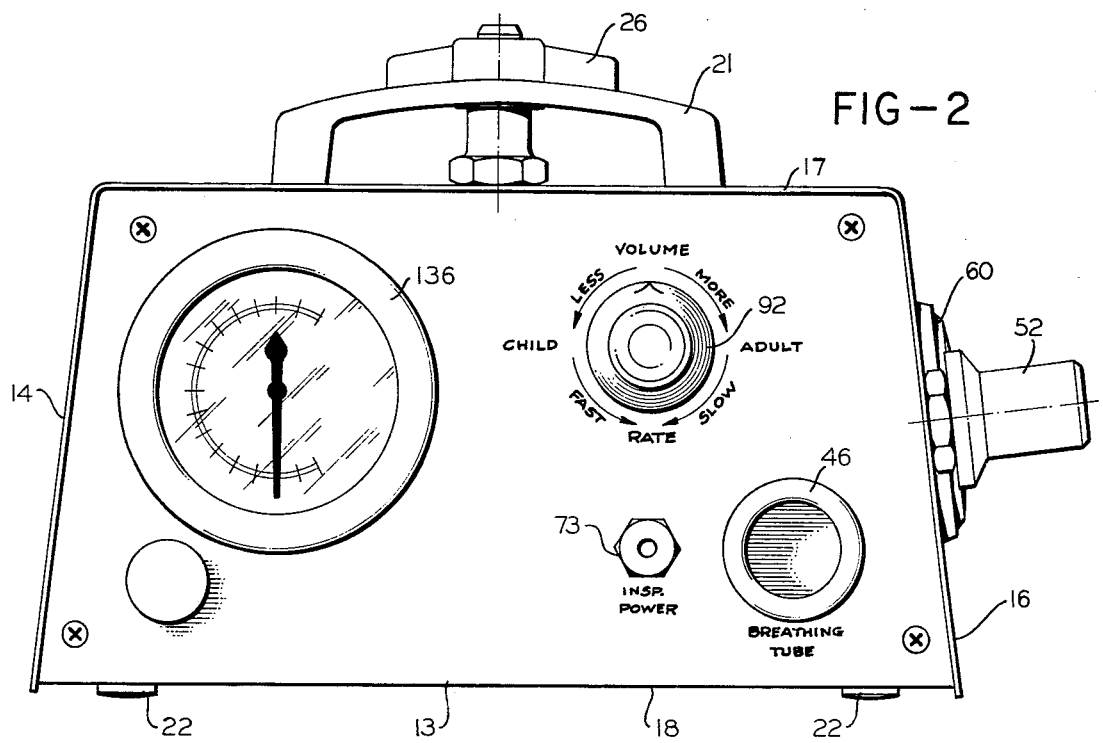
FIG. 2 is an enlarged front elevational view of the ventilator without the breathing tube and other accessories attached thereto.

The ventilator 11 shown in the drawings consists of a case 12 which has the configuration shown and which is provided with a front wall 13, inclined side walls 14 and 16, top and bottom walls 17 and 18, and a rear wall 19. A handle 21 is provided on the top wall to make it possible to readily carry the ventilator from one location to another. It is also provided with rubber feet 22 which are secured to the bottom wall 18.

An inlet fitting 26 is mounted in the top wall 17 and is adapted to be secured to a source of gas under pressure such as provided by the inlet hose 27. The hose 27 can be connected to a source of oxygen or air, or a combination of the same at a suitable pressure as, for example, 50 psi. Gas which is supplied through the inlet fitting 26 passes through an inlet filter 28 provided within the case 12. The outlet of the inlet filter is connected by a tube 29 to the inlet 30 of a master sequencing cartridge 31 having a cartridge body 32. The master sequencing cartridge body 32 is provided with an outlet 33. The cartridge body 32 is also formed with a flow passage 34 which establishes communication between the inlet 30 and the outlet 33. Valve means is provided for interrupting the flow through the flow passage 34 and thereby interrupting the flow from the inlet 30 to the outlet 33 and consists of a poppet valve or valve member 36 carrying an O-ring 35 which is adapted to engage a valve seat 37 (see FIG. 6) to interrupt the flow passage 34.

The poppet valve 36 is slidably mounted in the body 32 for slidable movement between open and closed positions with respect to the valve seat 37. Yieldable means is provided for urging the poppet valve 36 toward an open position and consists of a spring 38 having one end engaging the body and having the other end engaging the flanged poppet valve 36. A disk-like seal 39 which is retained within the body 32 by a retaining ring 41 seals the poppet valve from the remainder of the master sequencing cartridge. The poppet valve 36 is adapted to be moved towards a closed position by a button 42 slidably mounted in the retaining ring 41 and engaging the seal 39 in a region opposite the poppet valve 36. The button 42 is carried by the central portion of a diaphragm 43 retained within the body 36 by an end cap 44 which clamps the outer margin of the diaphragm 43 between the body and the cap. The end cap 44 is held in place by a retaining ring 45.

Means is provided for connecting the outlet of the master sequencing cartridge to a breathing tube outlet 46 which is mounted on the front panel or wall 13. Such means includes a tube 47 which is connected to the outlet 33 of the master sequencing cartridge 32 and is connected to the inlet 48 of a manifold 49 provided as a part of the inspiratory flow/volume control valve assembly 51. The valve assembly 51 is of a conventional type and is mounted in the side wall 16 and has a control knob 52 which is accessible from the outside of the case 12. The control knob 52 controls the adjustment of the orifice 53 in the manifold and supplies gas through an outlet 54 through a tube 56. The tube 56 is connected to the center jet 57 mounted in one end of the master venturi assembly 58. The master venturi assembly 58 is mounted on a breathing circuit manifold 59 which is mounted upon the rear side of the front panel 13 and is connected to the breathing tube receptacle 46. A gate valve 61 is provided within the breathing circuit manifold and yieldable means in the form of a spring 62 is provided for retaining the gate valve 61 in a normally closed position. An over-pressure relief valve assembly 63 is mounted on the breathing circuit manifold 59 adjacent the outlet 46 and is provided with a gate valve 64 which is normally held in a closed position by yieldable means in the form of a spring 66.

The manifold 59 is provided with another outlet 67 which is connected by a tube 68 to one side of a member 69 having a fixed nebulizer orifice 71 therein. The other side of the member 69 is connected to a tube 72 which is connected to an inspiratory service or power socket 73 mounted on the front panel 13.

A conventional patient breathing circuit 76 is connected to the breathing tube receptacle 46 and the inspiratory service socket 73 and, as shown, consists of a large tube 77 which is provided with a fitting 78 which is mounted by a friction fit within the breathing tube receptacle 46. The other end of the tube 77 is connected to a fitting 79 which is mounted in one end of a nebulizer 81 of a conventional type generally described in U.S. Pat. No. 3,172,406. The other end of the nebulizer 81 is connected to one leg of a tee 82. Another leg of the tee 82 has a patient adapter of a suitable type such as a face mask 83 mounted thereon.

An exhalation valve assembly 84 of a conventional type is mounted on the remaining leg of the tee 82. The exhalation valve assembly 84 is provided with a muffler 86. Means is provided for supplying gas under pressure to the exhalation valve to maintain the same closed during the inspiratory phase and includes a tube 87 which is connected to one leg of a tee 88. Another leg of the tee 88 is mounted in the nebulizer orifice of the nebulizer 81. The remaining leg of the tee 88 is connected by a tube 89 to the inspiratory service socket 73.

Means is provided for controlling the cycling of the master sequencing cartridge 32 to control the flow of gases to the breathing circuit 46 and the inspiratory service socket 73 and consists of a volume/rate control valve assembly 91 which is mounted on the front panel 13. It is of a conventional type and is provided with a control knob 92 which is accessible from the front panel for adjusting the flow of gas through an adjustable orifice 93 provided in the manifold 94 forming a part of the control valve assembly 91. The manifold 94 is provided with an inlet 96 which is connected by a tube 97 to one side of a member 98 having a fixed balance orifice 99 provided therein. The other end of the member 98 is connected by a tube 101 which is connected to tube 47 which is, in turn, connected to the outlet of the master sequencing cartridge 32.

The outlet 102 of the control valve assembly 91 is connected by tube 103 to a tee 104 mounted upon a physiologically triggering servo cartridge 106. The other leg of the tee 104 is connected by a tube 107 which is connected to one end of a balance reservoir 108. The other end of the balance reservoir 108 is connected by tube 109 to tee 110 mounted in the servo port 111 of the master sequencing cartridge 31 and in communication with a chamber 115 provided on one side of the diaphragm 43. The other leg of the tee 111 is connected by tube 112 to a one-way check valve assembly 113 which serves as an inspiratory/expiratory ratio check valve. The check valve assembly 113 is connected to a ratio calibration valve assembly 114 which is provided with an adjustable orifice 116. The valve assembly 114 is connected by tube 117 to the tube 101.

A filter 60 of a conventional type is provided which is connected to the master venturi 58 to supply atmospheric air to the master venturi so that it can be mixed with the gases being supplied through the jet 57. The filter 60 is mounted in the side wall 16 of the case 12.

The triggering servo assembly 106 is provided with means for dumping the terminal timing circuit which includes the tube 107 to ambient. Thus, the triggering servo is provided with a flow passage 121 which is open to ambient. The servo assembly 106 is provided with a valve member 122 movable between open and closed positions with respect to a valve seat 123 for interrupting communication between ambient and the tee 104. The valve member is provided with a valve stem 124 for guiding the same. The valve stem is connected to a diaphragm 126. The cartridge 106 is provided with means forming a chamber 127 on one side of the diaphragm so that when the chamber 127 is filled with gas, the diaphragm urges the valve member 122 towards a closed position. Means is provided for yieldably urging the valve member 122 into a normally closed position and includes a spring 128 which engages one side of the diaphragm 126. The other end of the spring is adapted to be engaged by an adjustable member 129 which can be adjusted in position by a control knob 131. The cartridge 106 is provided with a fitting 132 which is in communication with the chamber 127 and which is connected by tube 133 to the breathing circuit manifold 59. The tube 133 is connected by another tube 134 to a manometer 136 which is mounted on the front panel 13 to give an indication of the pressure in the tube 133.

Operation and use of the ventilator in performance of the method for use therewith may now be briefly described as follows. Let it be assumed that the ventilator 11 has been connected to a source of gas under pressure through the tube 27. As soon as source gas is supplied, the source gas is supplied through the fitting 26 through the filter 28 to the inlet of the normally open pneumatically servoed master sequencing cartridge 32. Gas will thus flow from the inlet 31 to the outlet 33 of the cartridge through the tube 47 to the manifold 49 of the inspiratory flow/volume control assembly 51. In addition, gas will be supplied through the tube 101 and the tube 117 to the outlet of the inspiratory/expiratory ratio calibration valve assembly 114 and to the inlet of the manifold 94 of the volume/rate control valve assembly 91 through the balance orifice 99. Gas flow which is metered through the volume/rate control valve assembly 91 is directed into the tee 104 and the inlet of the physiologically triggering servo assembly 106. Flow also passes through the tube 107 through the balance reservoir 108 to the chamber 41 of the normally open master sequencing cartridge 32.

During the dynamic inspiratory phase shown in FIG. 3, gas supplied to the inspiratory flow/volume control valve assembly 51 is supplied through the tube 68, through the fixed nebulizer orifice 71 to the inspiratory service socket 73, through the tube 89 to the tee 88 where gas is supplied to the nebulizer orifice for the nebulizer 81. The gas under pressure is also supplied to the exhalation valve assembly 87 to maintain the exhalation valve assembly in a closed position. The fixed nebulizer orifice 71 controls the rate of nebulization from the nebulizer. There is also gas flow from the manifold 49 through the outlet 54 through the tube 56 to the fixed orifice jet 57 of the master venturi assembly 58. Since the orifice in the master venturi 58 is fixed, the amount of gas passing through the master venturi is adjusted by controlling the rate of flow through the jet 57 by adjustment of the flow through the same by adjustment of the knob 52 and the orifice 53 controlled thereby. The gases passing from the jet 57 will cause additional ambient air to be entrained through the filter 60 and to be delivered through the master venturi assembly 58 to open the gate valve 61 and to deliver the same to the breathing tube receptacle 46. The gases from the breathing tube receptacle are then supplied through the large tube 77 through the main flow passage of the nebulizer 81, through the tee 82 and to the patient adapter in the form of a mask 83 where it is supplied to the patient during the inspiratory phase.

The length of the inspiratory phase is a function of the rate at which the volume/rate control metering valve assembly 91 allows gas flow into the terminal timing circuit which is connected to the tube 107 and which includes the balance reservoir 108 and the chamber 41 behind the diaphragm 39. By metering gas into the chamber 41 at a controlled rate, the pressure rise can be adjustably controlled. Thus, it can be seen that the more limited the flow through the adjustable volume/rate control assembly 91, the greater the time required to build up a servoing pressure behind the master sequencing diaphragm 39. The normally open master sequencing cartridge will be pneumatically closed when the servoing pressure against the diaphragm 43 exceeds the opening forces of the spring 38 combined with the piston effect of the inlet gases against the diaphragm seal 39.

The balance orifice 98 spreads the calibration of the volume/rate control valve assembly 91 over 320° of travel of the knob 92. The rate of flow into the terminal timing circuit is determined by the volume/rate control valve assembly 91. During the inspiratory phase, the inspiratory/expiratory ratio check valve assembly 113 is held competent by inspiratory gases back flowing against the inspiratory/expiratory calibration valve 114 to exert pressure against the outlet of the inspiratory/expiratory ratio check valve assembly 113.

The volume/rate control valve assembly 113 is stopped by cams (not shown) to provide minimum and maximum inspiratory time. It can be appreciated that if the valve assembly 91 were completely closed, an infinite inspiratory phase would be held which would be undesirable. The balance reservoir, although not essential, provides additional volume in the terminal timing circuit and permits the use of a less critical volume/rate metering valve assembly 91 for a wide range of functional ventilatory rates. In addition, since it provides a greater volume, there is a more gradual increase in pressure and a tapered effect in the closing of the master sequencing cartridge 31.

The flow of gases during the dynamic inspiratory phase is shown by the arrows in FIG. 3. The flow of gases during the dynamic expiratory phase is shown by arrows in FIG. 4 and the expiratory phase is initiated at the instant of closure of the normally open master sequencing cartridge 32. Closing of the master sequencing cartridge 32 interrupts the flow of gas from the source into the line 47. The remaining pressure of gases supplied to the manifold 49 rapidly decreases by bleeding off through the nebulizer orifice 71 and through the inspiratory service socket 73 and also through the adjustable orifice 53 through the jet 57 and into the breathing circuit 46. This pressure drop in the servoing circuit connected to the line 47 produces a reverse flow of gas from the timing circuit and from the line 107 through the restricted orifice 93 through the balance orifice 99 and into the line or tube 47.

During the expiratory phase, timing gases from the terminal timing circuit connected to the tube 107 are exiled by parallel routes. One route is through the adjustable metering orifice 93 of the volume/rate control valve assembly 91 and through the balance orifice 99 to the line 47. The other route is through the I/E check valve assembly 113 through the I/E ratio calibration valve assembly 114 through the tube 117, the tube 107, to the tube 47 where it is bled off through the breathing tube receptacle 46 and the inspiratory service socket 73.

Back flow through the volume/rate metering valve assembly 91 progressively reduces servoing pressures behind the diaphragm 39 of the master sequencing cartridge. This continues until the pressure in the chamber 41 drops to a suitable value as, for example, 7 to 8 psi in which the opening forces exceed the closing forces and the master sequencing cartridge 32 opens. As soon as the master sequencing cartridge opens, this mechanically starts the next dynamic inspiratory phase.

As can be seen, there is a differential between the opening and closing pressures of the master sequencing cartridge 32. The opening forces are due to a combination of the force applied by the spring 38 and the force which is applied by the pressure of the inlet gases against the seal 39.

The purpose of the parallel route for the exiled gases from the terminal timing circuit is to allow calibration of the inspiratory/expiratory ratios. The normal inspiratory/expiratory ratio of the timing circuit is established at approximately 1 to 15 but to allow the clinical option of ratios less than 1 to 3, or even greater than 1 to 3. The inspiratory/expiratory ratio check valve assembly 113 and inspiratory/expiratory ratio calibration valve assembly 114 serve as an expiratory bypass circuit. The basic expiratory time as referenced to inspiratory time is reduced by increasing the rate of expiratory outflow from the terminal timing circuit by progressively increasing the size of the orifice of the inspiratory/expiratory calibration valve assembly 114. Thus, while the basic inspiratory/expiratory ratio is established by the differential in opening pressure of the master sequencing cartridge 32 and the rate of inspiratory and expiratory flow across the volume/rate control metering valve, the inspiratory/expiratory ratio is calibrated by increasing the rate of flow from the expiratory circuit by the expiratory bypass loop.

Upon initiation of the expiratory phase, gas under pressure is no longer supplied to the inspiratory service socket 73 and permits the exhalation valve assembly 84 to open and to permit the patient to exhale to the atmosphere.

During the mechanical inspiratory phase and prior to the expiration of the expiratory timing period, the patient can trigger the ventilator into a mechanical inspiratory phase as shown in FIG. 5 to provide dynamic physiological triggering during the expiratory phase. This is accomplished by "dumping" the pressure between the volume/rate metering valve assembly 91 and the chamber 41 to the atmosphere during any part of the mechanical expiratory phase. Normally, the piston effect (opening pressure) against the valve member 122 is balanced by the spring 128 providing a closing force. Thus, a precise balance between the opening and closing forces can be adjustably established by adjustment of the knob 131. The large area diaphragm is superimposed between the valve member 122 and the spring 128 with the reference side of the diaphragm 126 being vented to ambient. The servoing side of the chamber 128 of the servo 106 is connected by the tube 133 to the breathing circuit manifold 59. During the positive pressure inspiratory phase, the diaphragm 126 is loaded with inspiratory gases to provide a closing force.

In the event that the patient exerts a breath during the inspiratory phase, a sub-ambient condition is created in the breathing tube receptacle 46 which is conveyed to the chamber 127. This creates an opening force to open the valve member 122 against the force of the spring 128 to vent the line or tube 127 to the atmosphere. By way of example, the spring 128 can be adjusted to permit the servo 106 to move to an open position when the physiological pressure drops between −2 and −3 cm of H$_2$O.

The gases within the terminal timing circuit are normally deadheaded in the tee 104 against the inlet of the physiologically triggered servo valve. Thus, it can be seen that as soon as pressure drop is created within the breathing circuit during the exhalation phase, the valve member 122 is moved to an open position to dump the terminal timing circuit to the atmosphere to cause the master sequencing cartridge 32 to instantaneously shift to the inspiratory phase.

With the ventilator it can be seen that the mechanical airway pressures are continuously monitored by the manometer 136. Peak pressure limiting is provided by an adjustable spring-loaded pressure relief valve with pressure governer assembly 63. Relieving pressure may reach about 65 cm of H$_2$O. However, if desired, this can be adjusted.

From the foregoing, it can be seen that there has been provided a ventilator and method in which a single control can be utilized to determine both the inspiratory and expiratory times and which can be utilized on human beings of all ages. The ventilator is one which is particularly useful in emergency medicine and which can be utilized by relatively unskilled personnel.

With the ventilator it is possible with one control valve to obtain flow rates which are satisfactory ranging from an infant to an adult. It is possible to maintain an almost constant inspiratory/expiratory time ratio from operative cyclic frequencies from over approximately 30 per minute down to approximately 5 per minute and to provide a volume of gas to the patient which is substantially inverse to the rate. In other words, at high frequencies, there is a small tidal volume and at low frequencies there is a large tidal volume which meet the requirements for an infant and an adult, respectively.

What is claimed is:

1. In a ventilator having an inhalation phase and an exhalation phase in its operative cycle for use with a source of gas under pressure, a master sequencing cartridge having an inlet adapted to be connected to the source of gas under pressure and an outlet, a valve member movable between open and closed positions for controlling the flow of gas from the inlet to the outlet, diaphragm means for moving said valve member from an open position to a closed position and forming first and second chambers in the cartridge on opposite sides of the diaphragm means, a breathing circuit outlet, breathing circuit means coupling the breathing circuit outlet to the outlet of the master sequencing cartridge, a single volume/rate control valve assembly having an inlet and an outlet with an orifice interconnecting the same and an adjustable needle valve disposed in the orifice, means coupling the inlet of the control valve assembly to the outlet of the master sequencing cartridge, means connecting the outlet of the control valve assembly to the first chamber on one side of the diaphragm means to bleed gas through the control valve assembly in one direction into said first chamber to move said valve member to terminate the inspiratory phase and initiate the expiratory phase and thereafter to bleed off gas from the first chamber through the control valve assembly in an opposite direction into the breathing circuit means whereby after sufficient bleed-off of gas from the first chamber the valve member moves to the open position to terminate the expiratory phase and initiate the inspiratory phase, and volume/rate control valve assembly including a single adjustable control means for the ventilator to control both the length of the inspiratory phase and the length of the expiratory phase such that an almost constant inspriatory expiratory time ratio from operative cyclic frequencies from over approximately 30 per minute down to approximately 5 per minute is maintained and a volume of gas to the patient which is substantially inverse to the rate is provided whereby, at high frequencies, there is a small tidal volume and at low frequencies there is a large tidal volume which meet the requirements for an infant and an adult, respectively.

2. A ventilator as in claim 1 together with a physiological triggering servo assembly, said servo assembly having an inlet coupled to the outlet of said volume/rate control valve assembly, an outlet open to ambient, a valve member movable between open and closed positions to control the flow of gas from the inlet to ambient, diaphragm means coupled to said valve member and means forming a chamber on one side of the diaphragm means and in communication with the breathing circuit outlet for sensing the pressure of gases in the breathing circuit outlet and means for adjusting the force which must be applied to the diaphragm to cause movement of said last named valve member to a closed position to terminate the flow of gas from the inlet to ambient.

3. A ventilator as in claim 1 wherein said means coupling the breathing circuit outlet to the outlet of the master sequencing cartridge includes an inspiratory flow/volume control valve assembly having an adjustable orifice therein.

4. A ventilator as in claim 1 wherein said master sequencing cartridge includes a sealing member for separating said valve member from said diaphragm, said sealing member being exposed to gas under pressure from the source of gas when the valve member has been moved to an open position so that the piston effect keeping the valve member in an open position is greater after the valve member has been opened than prior to the opening whereby there is a large differential between opening pressure of the valve member and the pressure required to close the valve member.

5. In a ventilator having an inhalation phase and an exhalation phase in its operative cycle for use with a source of gas under pressure, a master sequencing cartridge having an inlet adapted to be connected to the source of gas under pressure and an outlet, a valve member movable between open and closed positions for controlling the flow of gas from the inlet to the outlet, diaphragm means for moving said valve member from an open position to a closed position and forming first and second chambers in the cartridge on opposite sides of the diaphragm means, a breathing circuit outlet, breathing circuit means coupling the breathing circuit outlet to the outlet of the master sequencing cartridge, a volume/rate control valve assembly having an inlet and an outlet, means coupling the inlet of the control valve assembly to the outlet of the master sequencing cartridge, means connecting the outlet of the control valve assembly to the first chamber on one side of the diaphragm means to bleed gas through the control valve assembly in one direction into the first chamber to move said valve member to terminate the inspiratory phase and initiate the expiratory phase and thereafter to bleed off gas from the first chamber through the control valve assembly in an opposite direction into the breathing circuit outlet whereby after sufficient bleed-off of gas from the first chamber the valve member moves to the open position to terminate the expiratory phase and initiate the inspiratory phase, said volume/rate control valve assembly serving as a single control for the ventilator to control both the length of the inspiratory phase and the length of the expiratory phase and an additional flow path means coupled between said first chamber and said breathing circuit means for bleeding off gas from said first chamber to said breathing circuit outlet and including a one-way check valve for only permitting flow of gas from said first chamber and an adjustable control valve in series with said one-way check valve for controlling the rate of flow of gas from said first chamber to thereby make possible adjustment of the ratio of the length of the inspiratory phase to the length of the expiratory phase.

6. A ventilator as in claim 5 together with a balance reservoir connected between the outlet of the volume/rate control valve assembly and said first chamber and a balance orifice connected between said additional flow path means and the inlet of said control valve assembly.

7. In a method for controlling the inhalation phase and the exhalation phase in the operative cycle of a ventilator supplied with gas from a source of gas under pressure by the use of a single adjustable volume/rate control valve assembly in conjunction with a master sequencing cartridge having a diaphragm operated valve member for controlling the flow of gas to the patient with a normally open position and a chamber on one side of the diaphragm for receiving gas to move the diaphragm operated valve member to a closed position, initiating the flow of gas from the source of gas to the master sequencing cartridge bleeding gas from the source of gas at a controlled rate through the single volume/rate control valve assembly in one direction into the chamber to move the valve member to a closed position to terminate inspiratory flow, bleeding gas from the chamber at a controlled rate through the single volume/rate control valve assembly in an opposite direction to terminate the expiratory flow using the differential in opening and closing pressures for the diaphragm operated valve member to obtain a ratio between inspiratory and expiratory times and bleeding off additional gas from the chamber through a passage independent of the single volume/rate control valve assembly to adjust the ratio of the length of the inspiratory phase to the length of the expiratory phase.

8. A method as in claim 7 together with the step of applying additional pressure to the diaphragm operated valve means to keep it in an open position after it has been moved to an open position.

* * * * *